United States Patent [19]

Branco et al.

[11] Patent Number: 4,665,648
[45] Date of Patent: May 19, 1987

[54] FILM-FORMING COMPOSITIONS FOR ENVELOPING GRAINS AND SEEDS

[75] Inventors: Bernard Branco, Le Chesnay; Michel Malandain, Marly Le Roe, both of France

[73] Assignee: Seppic SA, Paris, France

[21] Appl. No.: 823,458

[22] Filed: Jan. 28, 1986

Related U.S. Application Data

[60] Continuation-in-part of Ser. No. 666,762, Oct. 31, 1984, Pat. No. 4,576,646, which is a division of Ser. No. 627,665, Jul. 3, 1984, Pat. No. 4,513,019.

[30] Foreign Application Priority Data

Jul. 6, 1983 [FR] France ................. 83 11276

[51] Int. Cl.$^4$ .................. A61K 9/36; C08L 1/00; A01C 1/06
[52] U.S. Cl. ........................................ 47/57.6; 47/56; 47/74; 106/163.1

[58] Field of Search ............................ 47/57.6, 56, 74

[56] References Cited

U.S. PATENT DOCUMENTS

| | | | |
|---|---|---|---|
| 4,068,602 | 1/1978 | Mickus | 47/57.6 |
| 4,344,979 | 8/1982 | Gago | 47/57.6 |
| 4,513,019 | 4/1985 | Branco et al. | 427/3 |
| 4,576,646 | 3/1986 | Branco et al. | 106/163.1 |

*Primary Examiner*—Theodore Morris
*Attorney, Agent, or Firm*—Dennison, Meserole, Pollack & Scheiner

[57] ABSTRACT

The present invention relates to film-forming compositions for enveloping grains and seeds, comprising by weight:

15 to 85% of a cellulosic film-forming substance,
10 to 70% of at least one alpha cellulose,
1 to 30% of at least one plasticizer suitable for comsumption.

8 Claims, No Drawings

FILM-FORMING COMPOSITIONS FOR ENVELOPING GRAINS AND SEEDS

This application is a continuation-in-part of Ser. No. 666,762, now U.S. Pat. No. 4,576,646 filed Oct. 31, 1984, which is a divisional of Ser. No. 627,665, filed July 3, 1984, now U.S. Pat. No. 4,513,019. These applications are hereby incorporated by reference.

The present invention relates to film-forming compositions for enveloping solid forms, particularly grains and seeds; it also relates to a process for enveloping with said compositions and to products obtained, coated with these compositions.

In the field of grains and seeds, coating is the operation in which seeds of various shapes are treated to obtain seeds of a spherical and regular shape. This operation is generally carried out with fillers such as silica, kaolin, peat and cork and synthetic or natural polymer binders such as gelatin, polyvinyl alcohol, and cellulosic derivatives.

This coating operation is distinguished from the film-forming operation, in which coated or uncoated seeds are enveloped with a fine and even film. Film-forming has been carried out most often by powdering at the surface of the seeds, mixtures of pigments and phytosanitary treatment products. Film-forming can also be performed with polymer binders of different types such as acrylic and vinyl. These binders should be used cautiously since they tend to delay or prevent germination of seeds. Powdering on the other hand, has the disadvantages of poor adherence of the powder to the seed surface, and involving dust and treatment irregularities.

SUMMARY OF THE INVENTION

It is an object of the present invention to provide an improved composition for film-forming on coated and uncoated seeds.

It is a further object of the present invention to provide a composition for film-forming on grains and seeds which can be applied at a low temperature without damaging the grains and seeds and without affecting the germination thereof.

It is a further object of the present invention to provide a film-forming composition with high binding power which enables large quantities of phytosanitary products, organic and inorganic pigments, and mineral fillers to adhere to the surface of the grain.

To achieve these and other objects, the present invention provides a method for film-forming on grains and seeds comprising spraying on to the grains or seeds an aqueous solution or dispersion of a composition comprising, by weight, 15 to 85% of a cellulosic film-forming substance, 10 to 70% of at least one alpha cellulose, and 1 to 30% of at least one plasticizer.

DETAILED DESCRIPTION OF THE INVENTION

The cellulosic film-forming substances used according to the present invention are known materials which have previously been used in the coating art. Generally these materials may be selected from the alkylethers of cellulose, the hydroxyalkylethers of cellulose, the monocarboxylic esters of cellulose and the mixed ether esters of cellulose. The preferred cellulosics are hydroxypropylmethylcelluloses, hydroxpropyethylcelluloses, hyroxypropylcelluloses, and methylcelluloses, having a viscosity in a 2% by weight aqueous solution at ambient temperature of less than 60 cps.

The film-forming compositions of the present invention should contain at least about 15% by weight of the cellulosic film-forming substance. Contents of the film-forming substance less than about 15% by weight are insufficient to form a continuous film. In that case, the envelope, as seen by examination by microscope, is a simple juxtaposition of particles. On the other hand, with contents of film-forming substances greater than 85%, the envelope formed is similar to that of the prior art, presenting the problems known to the art.

The plasticizer used according to the present invention will preferably be one which is suitable for consumption. While the use of plasticizers with cellulosic film-forming substances is known, the essential function of the plasticizers in the present case is not to lower the melting point of the cellulosics, but rather to modify the suppleness and strength of the films made with these cellulosics. The plasticizer utilized may be a hydrophilic or hydrophobic product suitably selected to improve the suppleness of the film made.

Hydrophilic plasticizers make it possible to obtain films which are rapidly disintegrated in an acid medium or in water. Hydrophilic plasticizers which are suitable include glycerine, propylene glycol, polyethyleneglycol, sorbitol and saccharose.

Hydrophobic plasticizers make it possible to delay disintegration of the film. Suitable hydrophobic plasticizers include conventional fatty substances, such as alcohols, acids, fatty esters and derivatives thereof, and ethyl and butyl esters of phthalic, citric and sebacic acid.

The preferred plasticizers for coating grains and seeds are polyethylene glycols having a molecular weight of 400 to 6000, esters of fatty acids and polyethyleneglycol, and polyethoxylated fatty acids. One such preferred plasticizer is the stearate ester of polyoxyethylene 8, which is hydrodispersible and facilitates dispersion of the film-forming compositions of the present invention.

The film-forming compositions of the present invention will preferably contain at least 1% by weight (with respect to the dry film-forming substance) of the plasticizer. The plasticizer amount utilized for film coating of grains and seeds can be less than the amount which would be required in coating, for example, pharmaceutical tablets, due to the higher surface hardness of grain and seeds, and the lesser tendency for deformation. Moreover, when germination occurs, the film formed at the seed surface must crack easily to allow the plant to sprout through. A plasticizer content of more than 30% modifies the mechanical properties of the envelope formed, tending to make it too fragile.

The alpha celluloses which may be used in the compositions according to the present invention are preferably microcrystalline or fibrous alpha celluloses which are known to the art, and which have a mean granulometry of less than 100 microns, and preferably less than 60 microns. It is known that alpha celluloses are capable of performing the role of "binding agent" in products with OH functions and in particular, cellulosic derivatives, due to their propensity to create hydrogen bonds with other materials. In the present film-forming composition, the alpha cellulose also performs an important role in effecting good adherence of the coating film on the core seed or grain, which contains materials having OH functions.

The alpha cellulose content of the present film-forming compositions should be at least about 10%, since lower amounts do not give a binding power sufficient to modify the film-forming substance, and the film does not adhere well to the core. An alpha cellulose content greater than about 70% by weight, however, produces a film of insufficient pliability.

The compositions according to the invention may further comprise known additives conventionally used for modifying the properties of the coating material, such as may affect color or speed of dissolution, and additives for protecting the coating material, such as anti-oxidants and anti-ultra-violet additives.

The preferred process for utilizing the film-forming compositions according to the present invention comprises dissolving or suspending the various components of the composition in a suitable solvent such as an aqueous medium, and then spraying the solution or suspension obtained onto the previously prepared core grain or seeds. The aqueous solutions or dispersions may contain concentrations up to about 25% by weight of the film-forming composition, which enables coatings to be made in a short period of time, for example 15 minutes. The films obtained are very covering and adhere strongly to the solid substrate. Consequently, they present an excellent resistance to abrasion and peeling. Moreover, the hardness of the cores coated with these film-forming compositions is especially increased, and the films obtained are regular and may provide attractive colors with small quantities sprayed.

The film-forming compositions according to the present invention have a number of purposes other than simply increasing the hardness of the seeds and grains. These film-formers can be used to adhere phytosanitary, insecticidal, fungicidal and pigmented coatings to the grain and seeds. The pigmented products are especially useful in identifying the type of seed or grain and in checking the efficiency and regularity of the sowings. The coating followed by film-forming can also be used to diminish unevenness in the seeds to make the outflow from the sowing drills easier.

The quantity of fillers, phytosanitary products, and pigments which can be bound to the grains or seeds with the present film-forming compositions, can be as much as twelve times the weight of the film-forming composition itself without any tendency for powdering. By utilizing these fillers and other treatment products directly as coatings on the seeds, it is possible to modify the gloss of the color of the seeds and the sliding properties of the seeds. Coloration may also be added by adding a colorant adhering to the cellulosic film-former.

Another reason for the use of the film-forming composition is to maintain an effective protection against dampness while maintaining or improving the germinative properties of the seeds.

The film-forming compositions used in conjunction with seeds and grains will preferably be low temperature coating compositions.

The following examples will serve to illustrate the invention.

EXAMPLE 1

Film-forming on Onion Seeds

A film-forming composition containing 35 parts by weight hydroxypropylmethylcellulose (15 cps), 55 parts alpha cellulose (average particle size 20 microns), and 10 parts by weight polyethyleneglycol 6000 (PEG 6000) is prepared. The hydroxypropylmethylcellulose and the powdered alpha cellulose are first mixed for 4 minutes in a Lodige granulator. Then, a 20% solution of PEG 6000 in water is slowly added to the powder mixture to produce a composition having a granulometry of about 0.5 mm, which is homogeneous enough to avoid calibration. The granulate is removed from the granulator and is dried over a plate oven to produce the film-forming composition.

A pigmentary composition is prepared from 20 parts by weight blue phthalocyanine pigment, 40 parts titanium dioxide, and 40 parts talc. The powder mixture is introduced in a mixture of 190 parts water with 10 parts polyethoxylated nonylphenol. This mixture is then ground in a horizontal ball crusher to produce a blue fluid paste having about 35% solids.

A coating composition is prepared by introducing 10 parts by weight of the above formed film-forming composition into 78 parts water with stirring. After 20 minutes, a homogeneous suspension is obtained to which is added 12 parts by weight of the pigmentary composition.

300 grams of onion seeds are placed in suspension in a tepid air stream in a Aeromatic fluidized bed system provided with a spraying system. The air intake temperature of the fluidized bed is 55° C. while the exiting air temperature is 30° C. The coating composition is sprayed onto the onion seeds at a rate of 16 grams per minute at a spraying pressure of 2 Kg/cm$^2$. Coating takes place over a period of 12 minutes during which a quantity of coating composition equal to 8% of the starting weight of the onion seeds is sprayed. The resultant coated seeds are uniformly and homogeneously blue in color. Germination tests demonstrate that the seeds are not affected by the coating treatment.

EXAMPLE 2

Film-forming on Coated Lettuce Seeds

A film-forming composition is prepared by mixing together 30 parts by weight hydroxypropylmethylcellulose (15 cps), 60 parts by weight microcrystalline alpha cellulose, and 50 parts by weight talc in a granulator. 10 parts by weight polyethyleneglycol 6000 in a 20% aqueous solution is added to the granulator along with 50 parts by weight of a yellow pigmentary dispersion comprising 50% yellow iron oxide. The granulate produced is dried as in Example 1, and is dispersed in 700 parts by weight water by stirring for 20 minutes. 100 parts by weight of a phytosanitary paste (50% actives) is then added to the dispersion, the paste comprising a mixture of insecticide and fungicide. This produces a coating composition containing about 3% hydroxypropylmethylcellulose, 1% polyethyleneglycol 6000, 6% microcrystalline cellulose, 2.5% pigment, 5% talc, and 5% phytosanitary products, for a total of about 22.5% solids.

Lettuce seeds are initially rendered spherical by coating with a mixture of clay, kaolin and polyvinyl binder. The coated seeds weigh 1.5 kg. The film-forming composition is applied to the seeds in a conventional 40" diameter turbine rotating at 15 rpm. The lettuce seeds are maintained at 30° C. Spraying of the film-forming composition takes place with a Binks 460 "Airspray" spraying gun at a rate of 12 grams per minute and a pressure of 2 kg/cm$^2$. Coating takes place for 30 minutes, during which time an amount of film-forming composition equal to 8% of the weight of the seeds is applied. The seeds are dried with a hot air generator with an adjustable power of 200 to 800 watts. A yield of about 85% seeds with film formed is obtained, with the seeds being yellow in color, slightly glossy and homogeneous. The germination of these seeds is identical to that of seeds without the film.

EXAMPLE 3

Film-Forming on Maize Seeds

A film-forming composition is prepared from:
20 parts of methylcellulose, 15 cps
60 parts of cellulose powder, average particle size 60 microns
2 parts of polyethylene glycol 400
14 parts of talcum
4 parts of iron oxide yellow.
by the following process: 5 kg of methylcellulose, 15 cps, is mixed with 15 kg of cellulose powder, average particle size is 60 microns, and 3.5 kg of talcum in a DIOSNA granulator having a volume of 100 l.

An aqueous dispersion is prepared in a high-speed disperser with 500 g of PEG 400 and 1 kg of iron oxide yellow in 10 liters of water. This dispersion is added to the powder in the DIOSNA granulator.

Granulation of the mixture is then carried out with 1.5 liters of water, using the high-speed to uniformize the particle size of granules which are formed. The granules are then dried in an oven for 9 hours at 80° C.

The resultant granulates are yellow, and have a particle size between 0.2 and 3 mm.

150 g of these granules are easily dispersed in 850 g of water, under moderate stirring for 20 minutes. A homogeneous suspension of 350 cps viscosity is obtained. 150 g of phytosanitary product (based on captane/anthraquinone) are added to the suspension to obtain a coating composition.

1.5 kg of maize seeds are put in a conventional pan of 40 cm diameter, and 44 g of the coating composition are sprayed, using a Binks 460 air-spray gun, on the 1.5 kg of maize in rotation in the pan over a period of 4 minutes. A uniform and slightly glossy coating is obtained on the seeds.

The total deposit on the seeds is 0.4% by weight of the phytosanitary product and 0.4% by weight of the dry substance of the film forming product, relative to the weight of the coated seeds.

What is claimed is:

1. Seeds or grains having a coating thereon, said coating comprising, by weight, 15 to 85% of a cellulosic film-forming substance, 10 to 70% of at least one alpha cellulose, and 1 to 30% of at least one plasticizer.

2. Seeds or grains according to claim 1, wherein said cellulosic film-forming substance is selected from the group consisting of alkylethers of cellulose, hydroxyalklyethers of cellulose, monocarboxylic esters of cellulose, and mixed ether esters of cellulose.

3. Seeds or grains according to claim 2, wherein said cellulosic film-forming substance is a hyroxpropylmethylcellulose having a viscosity of less than 60 cps at ambient temperature in a 2% by weight aqueous solution.

4. Seeds or grains according to claim 1, wherein said alpha cellulose is a microcrystalline or fibrous alpha cellulose having an average granulometry less than 60 microns.

5. Seeds or grains according to claim 1, wherein said plasticizer is selected from the group consisting of polyethyleneglycols of molecular weight 400 to 6000, esters of fatty acids and polyethyleneglycol, and polyethoxylated fatty acids.

6. Seeds or grains according to claim 1, wherein said coating additionally comprises at least one additional substance selected from the group consisting of fillers, pigments, and phytosanitary products.

7. Seeds or grains according to claim 6, wherein said phytosanitary products are selected from the group consisting of insecticides, fungicides, and mixtures thereof.

8. Seeds or grains according to claim 1 which are rendered spherical by an initial coating thereon.

* * * * *

UNITED STATES PATENT AND TRADEMARK OFFICE
CERTIFICATE OF CORRECTION

PATENT NO. : 4,665,648
DATED : May 19, 1987
INVENTOR(S) : Bernard Brancq; Michel Malandain It is certified that error appears in the above-identified patent and that said Letters Patent are hereby corrected as shown below:

On the Title Page, Item [75] "Branco" should read -- Brancq --.

Signed and Sealed this

Eleventh Day of August, 1987

*Attest:*

DONALD J. QUIGG

*Attesting Officer*      *Commissioner of Patents and Trademarks*